(12) United States Patent
Shrivastava et al.

(10) Patent No.: US 8,709,506 B2
(45) Date of Patent: Apr. 29, 2014

(54) SYNERGISTIC COMPOSITIONS FOR THE TREATMENT OF TOPICAL VIRAL INFECTIONS

(75) Inventors: Ravi Shrivastava, Cebazat (FR); Christiane Shrivastava, Cebazat (FR)

(73) Assignee: Vitro Bio Sarl, Issoire (FR)

( * ) Notice: Subject to any disclaimer, the term of this patent is extended or adjusted under 35 U.S.C. 154(b) by 0 days.

(21) Appl. No.: 13/521,669

(22) PCT Filed: Jan. 11, 2010

(86) PCT No.: PCT/EP2010/050236
§ 371 (c)(1),
(2), (4) Date: Oct. 1, 2012

(87) PCT Pub. No.: WO2011/082835
PCT Pub. Date: Jul. 14, 2011

(65) Prior Publication Data
US 2013/0028995 A1    Jan. 31, 2013

(51) Int. Cl.
*A01N 65/00* (2009.01)

(52) U.S. Cl.
USPC .......................................................... 424/725

(58) Field of Classification Search
None
See application file for complete search history.

(56) References Cited

FOREIGN PATENT DOCUMENTS

WO          02094300 A1     11/2002

OTHER PUBLICATIONS

International Search Report dated May 17, 2010 for corresponding International Application No. PCT/EP2010/050236, filed Jan. 11, 2010.

Schwerdtfeger et al., "Wirkung von Pflanzenextrakten auf die Neuraminidase-Aktivitat—Effects of Plant Extracts on Neuraminidase Actvity" Zeitschrift Fuer Phytotherapie, Hippokraptes Verlag in MVS Medizinverlage, De Lknd—DOI: 10.1055/S-2008-1077269, vol. 29, No. 2, Jan. 1, 2008.
Fukuchi K. at al., "Inhibition of Herpes Simplex Virus Infection by Tannins and Related Compounds" Antiviral Research, Elsevier BV, NL, LNKD-DOI:10.1016/0166-3542(89)90038-7, vol. 11, No. 5-6, Jun. 1, 1989, pp. 285-297, XP023893379.
Saller R. et al., "Combined Herbal Preparation for Topical Treatment of Herpes Labialis" Forschende Komplementaermedizin—Klassische Naturheilkunderesearch in Complementary and Classical Natural Medicine, Karger, De LNKD-DOI:10.1159/000057255, vol. 8, No. 6, Jan. 1, 2001, pp. 373-382, XP009039163.
Quan et al., "Ginseng and Salviae Herbs Play a Role as Immune Activators and Modulate Immune Activators and Modulate Immune Responses During Influenza Virus Infection" Vaccine, Elsevier Ltd, GB LNKD-DOI:10.1016/J. Vaccine. 2006.07.041, vol. 25, No. 2. Dec. 8, 2006, pp. 272-282, XP005798941.
Rowe Cheryl A. et al., "Specific Formulation of *Camellia sinensis* Prevents Cold and Flu Symptoms and Enhances Gamma Delta T Cell Function: A Randomized, Double-Blind, Placebo-Controlled Study" Journal of the American College of Nutrition vol. 26, No. 5, Oct. 2007, pp. 445-452, XP002581999.
Koleckar Vit et al., "Condensed and Hydrolysable Tannins as Antioxidants Influencing the Health" Mini Reviews in Medicinal Chemistry, Bentham Science Publishers, Hilversum, NL, vol. 8, No. 5; May 1, 2008, pp. 425-447, XP009133408.
International Preliminary Report on Patentability and English translation of the Written Opinion dated Jul. 17, 2012 for corresponding International Application No. PCT/EP2010/050236, filed Jan. 11, 2010.

*Primary Examiner* — Michael Meller
(74) *Attorney, Agent, or Firm* — David D. Brush; Westman, Champlin & Koehler, P.A.

(57) ABSTRACT

A synergistic composition comprising plant extracts rich in tannins for the treatment of topical viral infections. The plant extracts contain at least one protease inhibitor and/or at least one viral glycoprotein inhibitor.

5 Claims, No Drawings

SYNERGISTIC COMPOSITIONS FOR THE TREATMENT OF TOPICAL VIRAL INFECTIONS

CROSS-REFERENCE TO RELATED APPLICATIONS

This application is a Section 371 National Stage Application of International Application No. PCT/EP2010/050236, filed Jan. 11, 2010, which is incorporated by reference in its entirety and published as WO 2011/082835 on Jul. 14, 2011, in English.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The present disclosure concerns a synergistic composition of plant extracts rich in tannins, said composition of plant extracts having synergistic inhibiting properties on proteases and viral glycoproteins. It also concerns a medicament comprising said synergistic composition for topical application to treat any viral infection. The term topical refers to all external parts of the body such as the skin, mouth cavity, throat, upper respiratory tract, nasal cavity, vaginal mucosa, eye surface and the natural body openings. The present disclosure thus relates to the treatment of viruses infections which are manifested on the body surface such as the oral and genital herpes, throat influenza virus infections, human papilloma virus, and other topical skin viral infections.

BACKGROUND

Topical viral infections are very common in human beings as the first viral entry into the body is often through virus contact with the external body surface.

A virus is a very small infectious agent with varying diameter between 10 to 300 nanometers and varying length up to 1400 nm (filoviruses) or more. The viruses can reproduce only inside the host cell.

All viruses have genes made from either DNA or RNA, and a protein coat that protects these genes. Some viruses have an envelope of fat that surrounds them when they are outside the host cell.

Although the mechanism of viral entry into the host cell varies among different virus groups, all viruses follow three basic steps to infect the host cell and to reproduce. Once the virus comes in contact with a host cell, the first step is the viral attachment to the host cell (initial infection), the second is the replication of viral genome inside the cell (virus multiplication) and the third is the exit of newly generated virus particles from the host cell.

The mode of progression of a topical viral infection is completely different than a systemic viral infection.

During a topical external infection such as the influenza virus, initially a few virus particles come in contact with a few cells on the skin or the mucus membrane and enters the cells. In some cases, the virus may be present in the body as a latent virus which migrates towards the skin or the mucus membrane. For example, in case of labial or genital herpes virus infection, the latent virus present in the nerve cells migrates towards the labial skin or towards the vaginal mucosa and start multiplying in a few cells. In other cases, once entered, some viruses can remain dormant into the cells (such as Herpes I and II into the nerve cells), and create the disease once the body defense mechanisms are dull. In all cases, there are practically no clinical signs at this stage.

After initial infection, the virus multiplies in a few cells and millions of new virus particles are then liberated topically and they start attacking new cells to create visible lesion. The same process occurs for the throat viral infections with the exception that the initial virus particles are not stored in the body but are inhaled by the host person.

The virus envelope has an important role for virus initial infection.

The virus envelope is associated with several proteins (glycoproteins) of the surface coat.

Glycoproteins of the surface coat are transmembrane proteins, anchored to the envelope by a hydrophobic domain. They are visible on the virus surface. Virus uses these glycoproteins to attach to the cell membrane and to enter into the host cell.

The virus envelope is a highly complex structure containing many types of glycoproteins. For example the herpes simplex virus (HSV 1 and 2) contains surface glycoproteins such as gB, gD, gH, gL, gC, gI, gE as main proteins. To infect the cells, currently it is postulated that the C and/or B glycoproteins (gC and gB respectively) and probably the gH glycoprotein, bound to the heparan sulfate receptors on the cell surface, to fuse with the host cell membrane and to create an opening or pore, through which the virus enters the host cell. Therefore, cells that are devoid of heparan sulfate receptors are not susceptible to HSV (Natalia Chesenko, 2002). This specificity determines the host range of a virus.

The differences in the surface glycoprotein structures confer different morphology and antigenicity in the same family of virus. For example, three different types of influenza virus, dubbed A, B, and C have been identified with HA (hemagglutinin) and NA (neuraminidase) as main surface glycoproteins. 13 major types of HA and 9 major antigenic determinants of NA have already been identified. This shows that the viral capsid may contain a very large variety of glycoproteins on the surface coat. It also means that each type of virus has its own way to facilitate cell attachment and cellular entry.

All the viral glycoproteins are not yet discovered and there is continuous research on the presence of new virus glycoproteins and their role in viral multiplication and infection. Continuous discovery of new virus surface glycoproteins, their role in host cell infection and frequent viral mutations makes the development of a specific topical antiviral drug nearly impossible.

In the absence of any specific antiviral drug, vaccines are currently considered the best antiviral therapy.

Vaccines may contain virus glycoprotein subunits but they have poor immunity as all the glycoproteins are not represented in a vaccine and their antigenicity is variable.

The whole inactivated virus vaccines are more efficient but can be prepared only for small and highly antigenic viruses.

Live virus vaccines with reduced viral pathogenicity are good immunogens but are unstable, dangerous (live viruses) with a risk of reversion to virulence.

Unfortunately due to complex surface glycoprotein structures, vaccines cannot be developed for many viruses such as the, HIV, herpes, papilloma virus and many others.

Most of the antiviral treatments are directed to interfere with intracellular virus multiplication process but have no effect at all on free virus particles, when the virus particles are present on the skin lesions (labial herpes for example), vaginal mucosa (genital herpes for example), or throat surface (influenza for example).

All the currently available antiviral drugs are directed to stop intracellular virus growth once the infection is already established. For example, intracellular nuraminidase inhibitors are used to treat the influenza, A, B and C type of enveloped viruses with 2 main classes of drugs by oral route:
- the adamantanes which interfere with viral uncoating inside the cells and are effective only against influenza A type of viruses;
- the newer class Zanamivir or Oseltamivir (Tamiflu) which interfere with the release of intracellular progeny viruses and require early oral administration to stop further virus growth.

To treat systemic herpes virus infection, different types of Acycloguanosines (Aciclovirs®) are used and are marketed under trade names such as Zovirax®, Ciclovir®, Herpex®, Acivir®, Acivirax®, Aciclovir® and Zovir®. These are nucleoside analogues which interfere with virus growth inside the cells but have no effect on the free virus on the surface of the body as these drugs are transmitted through the circulation and cannot reach the free virus particles present on the open viral lesions.

Furthermore, as the entire antiviral drugs act by interfering with normal cellular metabolic functions, they often induce severe toxic effects. Oral administration of Acyclovirus® and Famciclovir® for the treatment of labial herpes, genital herpes, herpes zoster and chickenpox may induce nausea, vomiting, diarrhea, headache, rashes, kidney damage and confusion; Amantadine® for the treatment of influenza A may cause nausea, loss of appetite, nervousness, light headache, unsteadiness, sleepliness, and confusion; Cidofovir®, Ganciclovir® and Foscarnet® for the treatment of cytomegalovirus may produce kidney damage and low white blood cell count; interferon-alpha given to stimulate immunity against viral infections may cause flu like symptoms, anaemia, depression, low white blood cell count, low platelet count; Oseltamivir® for the treatment of influenza A & B is known to produce nausea, vomiting and dizziness, and Ribavirin® used for RSV infection in children may produce breakdown of red blood cells and anaemia (URBAN M, Merck Manual, 2009). Topically applied acyclovirus (Zovirax®, Penciclovir® Vidarabine®) for cold sores are not effective and have no severe toxic effects known.

Neutralizing the free virus particles topically on the body surface seems to be a very efficient alternative to stop the infection; however there is currently no vaccine available to stop topical viral infection, in particular at the stage of the initial infection, to avoid topical viral entry into the cells.

Recent scientific work also proves that in addition to the virus surface glycoproteins, proteases also play an important role in facilitating topical viral entry into the cell. The use of proteases during viral multiplication inside the cells was known but their involvement to facilitate the viral entry from external body surface, such as the herpes and the influenza virus entry from the skin lesions or from the throat surface, was discovered recently (Kido, 2007; Delboy, 2008).)

As protease have the potential to hydrolyze specific proteins, some viruses having no specific receptor on the surface to attach and to enter into the host cell, take the help of these proteases to break the cell wall and to enter into the cells.

Proteases, also known as proteinases or proteolytic enzymes, are a large group of enzymes found in or outside the cells, particularly in the vicinity of the damaged tissues and play a vital role in protein catabolism by hydrolysis of the peptide bonds that link amino acids together in the polypeptide chain.

Proteases are involved in the splitting of the protein molecules. Their main role is to break and to clean the proteinous debris generated during the tissue breakdown because such substances interfere with the tissue repairing process. They are essential to create a favorable environment for subsequent tissue repairs. Some of them can detach the terminal amino acids from the protein chain (exopeptidases, such as aminopeptidases, carboxypeptidases) while the others attack internal peptide bonds of a protein (endopeptidases such as trypsin, chemotrypsin, pepsin, papain, elastase).

There are hundreds of proteases found topically or inside the cells and can be divided into four major groups according to the character of their catalytic active site and conditions of action: serine proteinases, cysteine (thiol) proteinases, aspartic proteinases, and metalloproteinases or Matrix-Metallo-Proteins (MMPs). Attachment of a protease to a certain group depends on the structure of catalytic site and the amino acid (as one of the constituents), essential for its activity.

Many proteases may be found topically on a virus infected skin or mucus membrane such as pepsin, trypsin, chymotrypsin, subtilisin, cystin proteinase (cathepsin B,H,K,L,S), aspartic proteinase (cathepsin D), clotting factors, and matrix metalloproteins involved in the process of topical wound healing such as gelatinase A (MMP-2), gelatinase B (MMP-9), collagenase (MMP-1), collagenase 3 (MMP-13), stromelysin-1 (MMP-3), stromelysin-3 (MMP-11), MT-1 MMP (MMP-14), macrophase metalloelastase (MMP-12) and surely many others which are not yet discovered.

The analyses of different type of proteases present in the extra cellular matrix, in the virus lesions on the skin (example herpes labialis), on the mucus membrane (example genital herpes), and on the throat surface (example influenza virus) also indicate that there are many different type of proteases present at the site of tissue infection having specific proteolytic activity.

It is well established that many viruses use proteases to facilitate their multiplication inside the cells such as the HIV 1 protease which helps HIV-AIDS virus to multiply by cleaving newly synthesized polyproteins at the appropriate places to create the mature protein components of an infectious HIV virion. Without effective HIV protease, the HIV virion remains non-infectious.

Therefore, intracellular protease inhibitors such as Saquinavir®, Ritonavir®, Indinavir®, Nelfinavir® and several others were developed to block the HIV virus growth. These products are given orally, either alone or in combinations (example Liponivir® and Ritonavir®) to block HIV virus growth. But their use as a general antiviral is highly limited due to their toxicity, side effects and poor activity.

Some intracellular protease inhibitors such as Agenerase®, Crixivan®, Invirase®, Kaletra®, Lexiva®, Norvir®, Prezista®, Reyataz® and Vitacept® have already been authorized as anti-protease drugs and are used orally in combination with other antiviral drugs for the treatment of AIDS.

Unfortunately most of these protease inhibitors are proteins in nature and are easily destroyed by the natural proteases present in the wound (Patick et al. 1998) and therefore they cannot be used for topical viral infections.

All the future antiviral treatments are also directed to stop intracellular virus replication by oral administration such as new protease inhibitors, nucleoside RNA replicase inhibitors, integrase inhibitors, nucleoside reverse transciptase inhibitors, non-nucleoside reverse transcriptase inhibitors and cycloporin derivatives but due to their intracellular mode of action, their topical use to stop virus entry into the cell is not yet envisaged.

Due to their role in tissue repair, topical concentration of proteases increases markedly at the site of injury. As topical viral infections are usually not detected before the skin or the mucosa is damaged, the amount of proteases is very high in all the topical viral infections.

The influenza virus which infects more than 500 million people in the world every year, which initially comes in contact with the throat cells during inhalation, has no processing protease for the viral membrane fusion glycoprotein precursor and the virus cannot enter into the cells. This virus therefore uses proteases present on the surface of the respiratory tract to enter and to infect throat cells. At least 5 different processing proteases (trypsin-like) have already been identified in the airways (Kido, 2007). Initially, a few virus particles enter into the cells, multiplies and millions of new virus particles are then liberated onto the throat surface. All these virus particles need the help of proteases to enter into new healthy cells and to spread the infection. Therefore our body defense mechanisms liberate anti-proteases called secretory leukoproteases in the upper respiratory tract and the pulmonary surfactants in the lower respiratory tract to reduce the amount of free proteases available for viral entry. When proteases activity predominant over the activities of inhibitory compounds, virus infection cannot be stopped (Kido, 2004). Recent scientific research also indicate that other topical viruses such as the herpes virus which cause labial and genital herpes also take the help of some proteases to infect the cells.

It has been shown that the open herpes virus lesions, the level of MMP-2 and MMP-9 proteases increase during early infection (Martinez, 2004), that certain protease inhibitors reduce the activity of herpes virus (La Frazia, 2006), and that cellular proteases are involved in the pathogenicity of enveloped viruses (Kido 1996).

Taking into consideration the role of surface viral glycoproteins for viral attachment with the host cell and the use of proteases by the viruses to enter into the host cells, it is essential to find a method for treating topical viral infections by neutralizing virus surface glycoproteins and the corresponding proteases simultaneously.

Currently there is no known topical anti-protease inhibitor or virus surface glycoprotein inhibitor to block topical virus entry into the cells.

This may be related to the fact that as there are many proteases, each with a specific activity, it is extremely difficult to find a specific drug which can neutralize all the proteases.

In the absence of current knowledge regarding exact number of proteases present topically and their role in topical viral infection, only a non-specific protease inhibitor can block all the proteases.

Taking into consideration the amount of free virus particles present topically on an infected surface (in millions), an effective treatment should not only neutralize specific virus glycoproteins but should also minimize the amount of those proteases which facilitate viral entry into the cells.

In the absence of any specific drug to kill topical virus particles which continue infecting new cells, Acyclovir® containing creams are also now marketed for topical application but due to their intracellular mode of action Acyclovir® cannot act on free virus particles liberated topically in the lesion and which are present outside the cell. In all the topical viral infections, the free virus particles present on the surface of the lesion continue attacking new healthy cells from outside to spread the infection.

Some herbal preparations are also proposed to apply topically on viral lesions but the absence of widespread use of any such herbal drug itself proves that their efficiency is extremely limited and they cannot be considered as specific antiviral drugs.

For example, the use of Rhubarb with Sage plant extract was proposed for the treatment of herpes labials where clinical results showed the mean lesion healing time of 7.6 days with sage cream, 6.7 days with Rhubarb-sage cream and 6.5 days with Zovirax® (Saller et al 2001). The association of these two plant extracts reduced the herpes lesion healing time by approximately 12% compared to about 15% with Acyclovir® containing Zovirax® cream which is not at all satisfactory to consider the product as a specific topical herpes treatment.

A large number of plant extracts have also been tested using isolated in vitro cell culture models or on the specific virus attachment receptors but they were not considered sufficiently antiviral for further clinical trials or for further development as antiviral drugs.

Sulfated polysaccharides from sea algae were shown to interfere with HIV heparin receptor binding (Witvrouw, 1997); Epigallocatechin gallate from green tea was found to block gp120-cd4 binding of the HIV-1 virus in isolated cells (Hamza, 2006); the extracts of Chinese medicinal plants Prunella vulgaris and Rhizoma cibotte were shown to inhibit HIV-1 gp41 Six-helix bundle formation in vitro probably as a result of tannin interference with HIV-1 gp41 Six-Helix bundle formation (Liu, 2002); the extract of an Indian plant *Swertia* chirata was found to reduce HIV-1 grown in vitro indicating that some plant extracts were found to have some anti-viral activity but this topical antiviral effect is not enough to use the plant as an anti-viral drug.

Other natural substances such as propolis was also suggested to inhibit herpes simplex virus type II growth as the aqueous extract rich in phenyl carboxylic acid and poor in flavonoids and the ethanolic extract rich in flavonoids, both showed reduction in HSV-2 infectivity (Nolkemper, 2009).

As in all the topical viral infections the superficial skin or mucus cells initially liberate a large amount of free virus particles on the surface of the lesions and as this free virus attach new healthy cells, often with the help of various proteolytic enzymes, an ideal topical antiviral treatment should possess the following main properties:

- It should neutralize all the viral glycoprotein receptors which help the virus particles to enter into the cell so as to stop new cell infection.
- It should simultaneously neutralize all of the proteases present on the infected surface which may be used by the viruses to enter into the cell membrane.
- It should be non-irritant, non toxic to the skin or mucus cells and should be inexpensive.

SUMMARY

An embodiment of the present invention relates to a synergistic composition comprising plant extracts rich in tannins for the treatment of topical viral infections, the plant extracts containing at least one protease inhibitor and/or at least one viral glycoprotein inhibitor.

DETAILED DESCRIPTION OF ILLUSTRATIVE EMBODIMENTS

The synergistic composition according to an embodiment of the invention preferably comprises between 0.1 to 20%, particularly between 0.5% to 6%, and more particularly between 2% and 4% by weight of each plant extract relative to the total weight of the synergistic composition, particularly depending upon the concentration of tannins in the extract used.

Preferably, at least one protease inhibitor of the synergistic composition according to an embodiment of the invention is from a tannin rich plant extract chosen in the group comprising plant extracts from *Echinacea purpurea* and *Camellia sinensis* and at least one virus glycoprotein inhibitor of the synergistic composition according to an embodiment of the invention is from a plant extract chosen in the group comprising plant extracts from *Mimosa tenuiflora, Alchemilla vulgaris, Centella asiatica, Asculus hippocastanum, Acacia catechu* and *Salvia officinalis*

Said extracts can be prepared using traditional extraction techniques, well known by one skilled in the art. In particular, the extracts can be prepared using extraction techniques with solvents. Solvents used can be, water, alcohol, glycerol, ethylene glycol, preferably glycerol.

Before extraction, the plant can be crushed, or cut into pieces and can be fresh, frozen, dried or lyophylized.

It is possible to carry out several successive extractions until complete exhaustion of the active ingredient by the solvant used. The time of extraction varies according to solvent, the temperature and possibly the pressure used for extraction. In practice, this time can be limited to less than two hours for a profitable industrial exploitation.

Any part of the plant can be used to prepare the plant extracts according to an embodiment of the invention.

Preferably, the extract of *Alchemilla vulgaris, Centella asiatica, Echinacea purpurea* and *Asculus hippocastanum*, is an extract of at least one aerial part, and more preferably a whole plant extract, while the extract of *Mimosa tenuiflora* and *Acacia catechu* is a bark extract of the plant.

The term "aerial part of said plant", is intended to mean any part of the plant which is not underground. Aerial part of a plant, comprise leaves, fruits, flowers, stems, seeds, preferably the leaves and branches.

The term "whole plant extract" is intended to mean an extract of the whole aerial parts of a plant.

These extracts can be prepared using different methods as described in the review article written by Huie W Carmen (Huie, 2002).

Depending upon the plant extract and the method of preparation, the concentration of tannins may vary between 1 to 35%, particularly between 2 to 12% of condensed tannins. Some of the said plant extracts containing the desired quantities of tannins are sold, for example, by Martin Bauer Company at Valanjou in France.

Tannins can be considered as any phenolic compound of sufficiently high molecular weight containing sufficient hydroxyls and other suitable groups (i.e. carboxyl) to form effectively strong bonds with most of the macromolecules. Due to the protein binding properties of tannins they are used since ancient times to convert skin into hide as they create bonds between all the dead skin protein molecules converting the skin into leather.

Particularly, the extract of *Alchemilla vulgaris* according to an embodiment of the invention can comprise between 1 to 20%, preferably between 2 to 12% and more preferably between 3 to 8% by weight of tannins relative to the total weight of the extract, expressed in dry extract.

Particularly, the extract of *Mimosa tenuiflora* according to an embodiment of the invention can comprise between 1 to 25%, preferably between 2 to 14% and more preferably between 3 to 12% by weight of tannins relative to the total weight of the extract, expressed in dry extract.

Particularly, the extract of *Echinacea purpurea* according to an embodiment of the invention can comprise between 0.5 to 12%, preferably between 1 to 8% and more preferably between 2 to 7% by weight of tannins relative to the total weight of the extract, expressed in dry extract.

According to one embodiment, the synergistic composition of the invention comprises plant extracts rich in tannins from *E. purpurea* in association with plant extracts rich in tannins from *M. tenuiflora, A. vulgaris, C. asiatica* or *A. hippocastanum* for the treatment of herpes virus neutralization.

According to another embodiment, the synergistic composition of the invention comprises plant extracts rich in tannins from *E. purpurea* in association with plant extracts rich in tannins from *C. sinensis* for the treatment of influenza virus.

According to another embodiment, the synergistic composition of the invention comprises plant extracts rich in tannins from *C. sinensis* in association with plant extracts rich in tannins from *A. catechu* or *M. tenuiflora* for the treatment of influenza virus.

According to one embodiment, the synergistic composition of the invention comprise a plant extract rich in antiprotease activity, selected from *E. purpurea* or *C. sinensis* in synergistic association with a plant extract capable to neutralize viral glycoproteins, selected among the extracts from *M. tenuiflora, A. vulgaris, C. sinensis, C. asiatica, Asculus hippocastanum, Salvia officinalis,* or *Acacia catechu*. The extracts can be associated in a ratio of 1:1 w/w but this ratio can vary depending upon the type of viral infection to be treated.

Preferably, the synergistic composition is a composition for the treatment of topical viral infections chosen in the group comprising labial or genital herpes, influenza, throat infection, papilloma virus and other viral infections of the skin and mucus membranes.

As previously defined, the term "topical" refers to all external parts of the body such as the skin, mouth cavity, throat, upper respiratory tract, nasal cavity, vaginal mucosa, eye surface and the natural body openings. The synergistic composition of an embodiment of the present invention thus relates to a composition for the treatment of viruses infections which are manifested on the body surface such as the oral and genital herpes, throat influenza virus infections, and other topical skin viral infections.

The term "topical viral infections" are intended to mean all the topical infections where virus particles are present topically.

The term "synergistic" is intended to mean that the combined effect of the plant extracts rich in tannins of the composition is higher to the effect of each plant extract used alone.

An embodiment of the invention also relates to the use of the synergistic compositions of an embodiment of the present invention to manufacture a medicament or a medical device for the treatment of topical viral infections.

The term "medical device is intended" to mean any product (the association of plant extracts for example) or article that exerts its action mainly through its physical properties (for example, binding with the proteolytic enzymes or other proteins in the cavity of the injury) without affecting the functions of the body cells.

Medical device can include compression bandage, hydrogels, polymer films, solution, suspension, cream, gel, ointment, lotion, slow release devise, or a spray.

An embodiment of the invention also relates to a method of treatment of topical viral infections, comprising the step of administering to a subject a synergistic composition of an embodiment of the present invention.

An embodiment of the invention also relates to the non-therapeutic use of the synergistic composition of an embodiment of the present invention, as a cosmetic product for topical application on skin lesions of viral origin. Such cosmetic product can be a solution, suspension, cream, gel, ointment, lotion, slow release devise, film, or a spray. The proof of the synergistic antiviral properties of the association of two plant extracts in preventing and/or curing topical viral infections is apparent from the following pharmacological, toxicological and clinical studies. The presented examples illustrate embodiments of the invention, but they should not be considered to limit the scope of the invention in any way.

Summaries of the experiments presented by the Inventor include the steps of:
selecting plants,
preparing plant extracts,
selecting virus species,
testing and analyzing the protease inhibiting activity of the prepared plant extracts,
testing and analyzing the virus glycoprotein neutralizing properties of the prepared plant extracts,
testing the synergistic activity of plant extracts having antiprotease or virus glycoprotein inhibiting properties to neutralize virus,
clinical evaluation and safety assessment of the synergistic compositions.

Selection of Plants and Preparation of Plant Extracts:

134 tannin rich known plants were selected including *E. purpurea, Mimosa tenuiflora* (*M. tenuiflora*), *Asculus hippocastanum* (*A. hippocastanum*), *Salvia officinalis* (*S. officinalis*), *Alchemilla vulgaris* (*A. vulgaris*), *Centella asiatica* (*C. asiatica*), *Camilla sinensis* (Green tea), and *Acacia catechu* (*A. catechu*).

Plant extracts of the selected plants were prepared using the part of the plant which contains maximum amount of condensed tannins.

As hydrosoluble tannins are not suitable for topical application, plant extracts were enriched in condensed tannins using different extraction methods published in the literature (Nafisi-movaghar, 1991). Briefly, initially the plant material was mixed with water at 1:12 solid to water ratio and stirred between 200-300° F. at 2-50 Psi pressure for 1 hr. The aqueous solution obtained was than filtered through a polymeric membrane to remove large particles. The solution was purified by adding 3% bentonite w/w and removed by filtration. The extract was than kept in contact with an adsorbent material (non ionic resin packed in a column) and the tannins retained on the adsorbent material were eluted with a polar solvent. The concentrated tannins extract was then dried by atomization to obtain a tannin rich dried and soluble plant extract. The percentage of tannin in the dried extract varied between 5-34% depending upon the initial richness of the plant in tannins and the part of the plant used. Before use these dried extracts were solubilised in water (10 mg/ml) as mother solution. For experiments, each plant extract was further diluted at a final concentration of 1 mg/ml and at a final concentration of 0.5 mg/ml when two plant extracts were associated.

Selection of Reference Viruses:

Among topical viral infections, herpes virus inducing topical labial and genital lesions and the influenza virus causing throat infection, represent the major topical viruses possessing surface glycoproteins. Therefore these two viruses were taken as reference viruses for all the experiments.

Testing and Analyzing the Protease Inhibiting Activity of the Prepared Plant Extracts:

Research for the Proteases Involved in Viral Entry into the Cells:

In the absence of knowledge regarding the proteases involved in facilitating viral entry into the cells, initial experiments were conducted with different proteases to select those which are involved in facilitating the herpes and influenza virus entry into the cells. The selected Matrix Metalloproteins: MMP1, MMP2, MMP3, MMP7, MMP9, MMP10 and MMP12, were than tested in different associations to find all the MMPs involved in a particular virus entry.

The purified human MMPs (proteases) and the protease assay kits were purchased from AnaSpec, Inc, USA. The MMP 1 (interstitial and fibroblast collagenase, Ref. 72004 and 71128); MMP 2 (gelatinase A, Ref. 72005 and 71151); MMP 3 (stromelysin-1, transinl, Ref. 72006 and 71153); MMP7 (proenzyme, Ref. 72007), MMP-9 (gelatinase B, collagenase IV, Ref. 72009 and 71134) and MMP-12 (elastase, Ref. 72010 and 71137), MMP-10 (stromelysin 2 Ref. 72067 and 72024) were used at concentration of 0.5 µg/ml either with the viral suspension, with the cell culture and for the quantitative analysis.

Initially, Vero (African Green monkey kidney) and MDCK (Madine Durby Canin Kidney) cells were grown in 75 cm$^2$ tissue culture flasks (Corning, USA) in Dulbecco's Modified Eagle's Medium (DMEM) supplemented with 10% fetal calf serum (FCS) and antibiotics. All cells were cultivated at 37° C. with 5% $CO_2$. Experiments were conducted in cell cultures grown in 96-well tissue culture plates using serum free medium and appropriate controls.

Cell culture models where cells remain exposed to the external environment were used to mimic topical viral infections. Vero cells sensitive to herpes virus infection and MDCK cells sensitive to influenza virus infection were used.

Cells and viruses were purchased from ATCC culture collection, USA.

To determine virus titer and 50% tissue culture infective dose ($TCID_{50}$) or 100% tissue culture infective dose ($TCID_{100}$) cells were grown in confluency in 96-well tissue culture plates with 10-fold virus dilutions (m.o.i.2) and incubated at 37° C. for 1 h. After inoculums removal, cells were washed with PBS and incubated for 72 h. with fresh medium. Cell death was evaluated with MTT vital staining. In some cases, for influenza virus, a 50-µl sample of supernatant was drawn from each well, transferred to a new 96-well plate and virus was titrated by haemagglutination (HA) test with a 0.5% suspension of chicken red blood cells. The TCID doses were calculated by the method of Reed and Muench (1938).

To search the proteases involved in virus entry into cells, individual protease or an association of proteases (0.5 µg/ml) was exposed to cell cultures infected with $TCID_{50}$ concentration of herpes or influenza virus in a protease free, serum free tissue culture medium for 72 h. Virus growth was than determined as described previously.

If there was no change in virus growth, the MMP was considered not involved in the process of viral entry into the cells but if the virus growth was superior to the corresponding non MMP added virus controls, the percent increase in virus growth was determine to evaluate the extent of MMP involvement in virus entry into the host cells. Values represent mean of minimum 3 experiments (n=16 per experiment).

Only the results with the MMPs involved in herpes and influenza virus growth are presented below (Table 1):

| SN° | Type of Protease | % cell death after 72 h TCID$_{50}$ herpes virus infection | % increase in herpes virus growth compared to controls | % cell death after 72 h TCID$_{50}$ influenza virus infection | % increase in influenza viral growth compared to virus control |
|---|---|---|---|---|---|
| 1 | MMP-1 | 66.32 ± 7.11 | +8.43 | 47.76 ± 7.26 | +63.87 |
| 2 | MMP-2 | 73.6 ± 6.20 | +31.43 | 71.90 ± 8.21 | +49.14 |
| 3 | MMP-3 | 64.16 ± 4.29 | +7.57 | 44.12.12 ± 3.89 | −8.49 |
| 4 | MMP-9 | 78.2 ± 5.92 | +39.64 | 74.61 ± 8.26 | +54.76 |
| 5 | MMP-10 | 70.46 ± 5.41 | +25.82 | 52.19 ± 7.56 | +8.26 |
| 6 | MMP-12 | 67.12 ± 5.91 | +19.86 | 48.89 ± 4.39 | +1.41 |
| 7 | MMP-7 Trypsin1 | 57.10 ± 6.68 | +1.96 | 72.76 ± 5.96 | +50.92 |
| 8 | MMP 2 + 9 + 10 + 12 | 86.22 ± 7.48 | +53.96 | 65.12 ± 9.68 | +35.07 |
| 9 | MMP 1 + 2 + 9 | 67.54 ± 7.12 | +20.60 | 87.36 ± 8.78 | +81.20 |
| 10 | Other proteases | Comparable to controls | <10.0% | Comparable to virus controls | <10.0% |
| 11 | Virus control | 56.0 ± 2.3 | — | 48.21 ± 6.77 | — |

The results shown in Table 1 indicate that the proteases are involved in viral entry into the cells. MMP-2, MMP-9 facilitates herpes as well as influenza virus entry; MMP-10 and MMP-12 are more specific to herpes virus while MMP-1 and MMP-7 particularly help the entry of influenza virus. All other proteases studies have little or no effect on topical virus entry into the cells under the experimental conditions employed in this invention. The MMPs 2, 9, 10 and 12 were selected for further experiments on herpes virus while MMPs 1, 2 and 9 were selected for the influenza virus.

These results also indicate that specific proteases are involved in the entry of specific viruses.

Testing and Analyzing the Anti-Protease Activity of the Prepared Plant Extracts:

Different species of the most active plant species in the same family of plant were evaluated for their activities but only the results of the most active plant species are presented in the result section. For example, the plant extracts of *Echinacea purpurea* (*E. purpurea*), *E. angustifolia, E. pallida* were evaluated for their anti-protease or anti-virus glycoprotein inhibiting properties but only the results of the most active species, *E. purpurea* are presented in the results.

Initially, the maximum non cytotoxic concentrations of each plant were determined by exposing different type of cells with various plant extract concentrations. Only non-cytotoxic concentrations were used for experiments.

To evaluate the anti-protease activity of different tannin rich plant extracts, a fixed concentration of each plant extract (1 mg/ml for individual plant extract and 0.5 mg/ml for an association of two plant extracts) was pre-incubated for 1 h in a test tube with an association of those MMPs which were found to enhance the growth of either herpes virus or the influenza virus. The MMP association for the herpes and influenza viruses contained MMP 2, 9, 10, 12 and MMPs 1, 2, 9, 7, respectively. The concentration of each MMP was 0.5 μg/ml.

After 1 h pre-incubation, the plant extract—MMP suspension was exposed to cell cultures pre-infected before 1 h with $TCID_{100}$ concentrations of either herpes or the influenza viruses. The cells cultures were washed with protease and serum free medium to ensure that there are no free virus particles on the surface of the cultures. The untreated cells served as cell controls while only virus treated cells served as virus controls. It was assumed that if the plant extract neutralize a specific protease, the protease will not be available for virus entry into the cell thereby reducing the cell infection and consequently the cell death.

The virus controls induced 100% cell death in 72 h. The reduction in cell death compared to the virus controls was determined as mean values of minimum 3 experiments and considered as anti-protease activity of the tannin rich plant extracts either alone or in association.

Only the results of the plant extracts showing any protective activity on virus growth (anti-protease activity) is shown individually. The following results were obtained:

TABLE 2

| S. No. | Plant extract | Mean antiprotease activity % against: Herpes virus | Infuenza virus |
|---|---|---|---|
| 1. | Ep | 28.21 | 31.23 |
| 2. | Gt | 6.46 | 38.92 |
| 3. | Mt | 7.91 | 3.12 |
| 4. | Av | 1.13 | 0.0 |
| 5. | Ca | 8.21 | 12.26 |
| 6. | As | 2.12 | 9.56 |
| 7. | So | 6.32 | 13.56 |
| 8. | Ac | 11.3 | 16.29 |
| 9. | Others | <10% | <10% |
| 10. | Ep + Gt | 30.66 | 41.48 |
| 11. | Ep + Mt | 29.77 | 32.96 |
| 12. | Ep + Av | 34.61 | 27.55 |
| 13. | Ep + Ca | 22.61 | 18.71 |
| 14. | EP + As | 31.12 | 0.0 |
| 15. | Ep + So | 19.20 | 32.24 |
| 16. | Gt + Mt | 17.40 | 33.38 |
| 17. | Gt + Av | 0.0 | 21.24 |
| 18. | Gt + Ca | 7.55 | 32.92 |
| 19. | Gt + As | 0.0 | 35.54 |
| 20. | Gt + So | 8.71 | 26.29 |
| 21. | Ep + Ac | 29.32 | 33.78 |
| 22. | Gt + Ac | 9.66 | 28.68 |

TABLE 2-continued

| S. No. | Plant extract | Mean antiprotease activity % against | |
|---|---|---|---|
| | | Herpes virus | Infuenza virus |
| 23 to 131 | Other 112 individual plant extracts | <5.0% | <5.0% |

Note:
Ep. = E. purpurea,
Mt = M. tenuiflora,
Av = A. vulgaris,
Gt = C. sinensis,
Ca = C. asiatica,
As = Asculus hippocastanum,
So = Salvia officinalis,
Ac = Acacia catechu.

The results shown in Table 2 prove that among 131 plant extracts studied, only 8 plant extracts showed slight to moderate anti-protease activity. Among individual plant extracts, only the plant extract of E. purpurea was capable to exert an anti-protease activity on the proteases involved in the entry of herpes virus as well as the influenza virus and only the extract of C. sinensis was capable to inhibit the MMPs which enhance influenza virus entry into the host cells. Associating half the most active concentration of E. purpurea or C. sinensis with M. tenuiflora, A. vulgaris, C. asiatica, A. hippocastanum, S. officinalis, or A. Catechu induced a slight synergistic effect to neutralize proteases.

None of the plant extracts or associations of plant extracts showed 100% inhibition of herpes or influenza virus indicating that although some plant extracts neutralize these viruses, this activity is not enough to inactivate all the virus particles and therefore they cannot stop topical virus infection completely.

We also observed that different species of plant extracts in the same family of plants, have more or less similar anti-protease properties.

Testing and Analyzing the Virus Glycoprotein Inhibiting Activity of the Prepared Plant Extracts:

Certain topically infective viruses such as the herpes or influenza virus contains glycoproteins on the viral capsid. As the glycoproteins trigger virus attachment to the host cells for intracellular penetration and as certain plant tannins bind specifically to certain glycoproteins, our aim was to evaluate the virus glycoprotein binding potential of each plant extract. The virus glycoprotein inhibition is considered directly proportional to the anti-viral potential of plant extracts.

The experiments were conducted in vitro using virus suspensions of herpes or influenza virus ($TCID_{100}$ concentration) which were incubated with a fixed amount of tannin rich plant extract (1 mg/ml). The virus-tannin suspension was pre-incubated (37° C.) for 1 h to allow plant tannin+virus binding.

The MMP association for the herpes and influenza viruses containing MMP 2, 9, 10, 12 and MMPs 1, 2, 7, 9 respectively, was added in the culture medium of the healthy cells at a concentration of 0.5 µg/ml and the cells (Vero and MDCK cells for herpes or influenza virus, respectively) were than exposed to the pre-incubated plant—virus suspension. The amount of virus was determined after 72 h incubation. Untreated cells and only virus treated cells served as negative and positive cultures. The following results were obtained (Table 3)

| S. No. | Plant extract | Virus glycoprotein inhibition in vitro (% reduction in viral growth compared to controls) | |
|---|---|---|---|
| | | Herpes virus | Influenza virus |
| 1. | Ep | 7.62 | 11.58 |
| 2. | Gt | 2.49 | 6.63 |
| 3. | Mt | 22.76 | 18.96 |
| 4. | Av. | 32.49 | 21.84 |
| 5. | Ca | 13.14 | 5.12 |
| 6. | As | 7.62 | 24.52 |
| 7. | So | 27.72 | 21.86 |
| 8. | Ac | 8.71 | 29.26 |
| 9. | Others | <10% | <10% |
| 10. | Ep + Gt | 31.09 | 28.26 |
| 11. | Ep + Mt | 19.12 | 39.96 |
| 12. | Ep + Av | 51.24 | 24.33 |
| 13. | Ep + Ca | 54.56 | 28.39 |
| 14. | EP + As | 38.88 | 17.22 |
| 15. | Ep + So | 24.48 | 28.61 |
| 16. | Gt + Mt | 20.01 | 34.46 |
| 17. | Gt + Av | 7.26 | 29.38 |
| 18. | Gt + Ca | 11.91 | 46.64 |
| 19. | Gt + As | 18.64 | 42.37 |
| 20. | Gt + So | 27.54 | 34.56 |
| 21. | Ep + Ac | 32.46 | 24.71 |
| 22. | Gt + Ac | 16.98 | 37.52 |
| 23 to 131 | Other individual plant extracts | <5.0% | <5.0% |

(Ep. = E. purpurea, Mt = M. tenuiflora, Av = A. vulgaris, Gt = C. sinensis, Ca = C. asiatica, As = Asculus hippocastanum, So = Salvia officinalis, Ac = Acacia catechu).

The results in Table 3 demonstrate that although almost all the plant extracts tested for virus glycoprotein inhibition were rich in tannins, only a few plant extracts (<8 out of 131 tested) neutralized virus. This proves that only a few tannins are capable to bind with virus glycoproteins and this binding is specific.

There is no correlation between protease and viral glycoprotein binding properties of a plant extract as those extracts which were found to bind strongly with proteases (E. purpurea, C. sinensis) had nearly no viral glycoprotein binding potential while some other plant extracts which had no effect on proteases (M. tenuiflora, A. vulgaris, A. hippocastanum, S. officinalis, A. catechu) had a strong virus glycoprotein binding properties as they markedly reduced virus infecting potential after 1 h pre-incubation with the plant extract.

The extracts of M. tenuiflora, A. vulgaris and S. officinalis binds specifically to the herpes virus glycoproteins while the extracts of A. hippocastanum, A. catechu and A. vulgaris binds particularly to the influenza virus proteins.

E. purpurea and C. sinensis tannin rich plant extracts strongly inhibited protease activity but has no effect on viral glycoproteins indicating that the tannin-protease or tannin-virus glycoprotein binding is highly specific.

Surprisingly, the association of a protease inhibitor plant extract with a virus glycoprotein inhibitor plant extract is the most effective to stop viral replication as on one side the proteases are not available for viral entry and on the other side the viral glycoprotein is not free to attach to the host cell.

Testing the Synergistic Activity of a Combination of a Plant Extract Having Anti-Protease with a Plant Extract Having Virus Glycoprotein Inhibiting Properties to Neutralize Virus, The synergistic activity of an individual plant extract (1 mg/ml) alone or in combination with an other plant extract (0.5 mg/ml each) were evaluated.

The herpes virus suspension contained 0.5 µg/ml of MMP 2, 9, 10, and 12 while the influenza virus suspension contained 0.5 μg/ml of MMP 1, 2, 7 and 9 as a virus entry helping protease. These suspensions were pre-incubated with a fixed amount of either herpes or influenza viruses (TCID$_{100}$) for a period of 1 h before infecting the host cells.

The anti-protease and antiviral glycoprotein inhibiting effects of active plant extracts are also shown in the following table 4 for comparison.

The results clearly prove that the individual plant extracts of Ep and Gt possess moderate anti-protease activity while the plant extracts of Av, Mt, Ca, As, Ac and So have specific but minor virus glycoprotein inhibiting properties.

These activities of the individual plant extracts are not enough to block and to neutralize all the virus particles present on the surface of the cells.

The association of two plant extracts induces surprisingly a synergistic effect to neutralize almost all the virus particles in the medium.

This proves that a synergistic association of virus glycoprotein inhibiting plant with a protease inhibiting plant is essential to neutralize almost all the virus particles and is the best solution to treat topical viral infections.

The results of total antiviral activity are shown in Table 4. The best anti-herpes virus plant extracts being Ep+Mt, Ep+Av, Ep+Ca, Ep+As and Ep+Ac. The best anti-influenza virus synergistic association being Ep+Gt and Gt+Ac.

TABLE 4

| S. No. | Plant extract | Mean antiprotease activity in vitro against | | Virus glycoprotein inhibition in vitro | | Total Antiviral activity | |
|---|---|---|---|---|---|---|---|
| | | Herpes | Inf. | Herpes | Inf. | Herpes | Inf. |
| 1. | E.p | 28.21 | 31.23 | 7.62 | 11.58 | 46.42 | 39.26 |
| 2 | Gt | 6.46 | 38.92 | 2.49 | 6.63 | 32.50 | 36.91 |
| 3. | Mt | 7.91 | 3.12 | 22.76 | 18.96 | 29.26 | 26.84 |
| 4. | Av | 1.13 | 4.96 | 32.49 | 21.84 | 30.81 | 27.56 |
| 5. | Ca | 18.21 | 12.26 | 13.14 | 5.12 | 17.16 | 24.72 |
| 6. | As | 2.12 | 9.56 | 7.62 | 24.52 | 26.61 | 24.55 |
| 7. | So | 6.32 | 13.56 | 27.72 | 21.86 | 32.22 | 30.19 |
| 8. | Ac | 11.3 | 16.29 | 8.71 | 29.26 | 28.64 | 42.55 |
| 9. | Others | <10% | <10% | <10% | <10% | <10% | <10% |
| 10. | Ep + Gt | 30.66 | 41.48 | 31.09 | 28.26 | 46.31 | 94.26 |
| 11. | Ep + Mt | 29.77 | 32.96 | 19.12 | 39.96 | 96.31 | 58.36 |
| 12. | E.p + Av | 34.61 | 27.55 | 51.24 | 24.33 | 91.44 | 50.48 |
| 13. | Ep + Ca | 22.61 | 18.71 | 54.56 | 28.39 | 86.39 | 61.37 |
| 14. | Ep + As | 31.12 | 6.59 | 38.88 | 17.22 | 81.77 | 33.49 |
| 15. | Ep + So | 19.20 | 32.24 | 24.48 | 28.61 | 38.41 | 67.11 |
| 16. | Gt + Mt | 17.40 | 33.38 | 20.01 | 34.46 | 41.72 | 89.36 |
| 17. | Gt + Av | 4.78 | 21.24 | 7.26 | 29.38 | 64.16 | 52.30 |
| 18. | Gt + Ca | 7.55 | 32.92 | 11.91 | 46.64 | 38.37 | 71.13 |
| 19. | Gt + As | 4.36 | 35.54 | 18.64 | 42.37 | 41.52 | 74.76 |
| 20. | Gt + So | 8.71 | 26.29 | 27.54 | 34.56 | 43.39 | 65.91 |
| 21. | Ep + Ac | 29.32 | 33.78 | 32.46 | 24.71 | 78.31 | 29.55 |
| 22. | Gt + Ac | 9.66 | 28.68 | 16.98 | 37.52 | 36.31 | 82.15 |
| 23. to 35. | Association of 3 plant extracts | <25.0% | <25.0% | <25.0% | <25.0% | <25.0% | <25.0% |

(Ep. = *E. purpurea*, Mt = *M. tenuiflora*, Av = *A. vulgaris*, Gt = *C. sinensis*, Ca = *C. asiatica*, As = *Asculus hippocastanum*, So = *Salvia officinalis*, Ac = *Acacia catechu*).

Clinical Assessment

To evaluate the clinical efficacy of the synergistic associations of the plant extracts, formulations were prepared as given in the example numbers 3, 4, and 5 for the treatments of viral throat infection, labial herpes and genital herpes, respectively.

The clinical trials were conducted at the Nexus clinical research center in India on 60 patients each having visible lesions of throat infection, labial herpes and genital herpes. The studies were conducted in accordance with the requirements of the current ICH guidelines on good clinical practice and declaration of Helsinki (Tokyo 2004).

For throat infection, patients having symptoms of acute influenza and throat infection were selected.

Throat product was applied as a spray, 3-4 times a day for a maximum period of 10-days.

Throat swabs, clinical examinations, efficacy assessments and other biological parameters were recorded before treatment, 2 h after $1^{St}$ treatment and on the days 2, 3, 4, 7 and 10.

The results showed 66% reduction in the presence of throat infection on the day 1, 72% on the day 7 and 100% on the day 10. Bacterial count and expectorant amount was reduced progressively up to day 7. No local irritation, side effects or allergic reaction was noticed in any of the patients.

For labial herpes study, patients having recent visible oral herpes lesions were enrolled in the study. Test product was applied as 3-4 drops of product directly on the lesion, 4-5 times a day up to complete healing. The amount of topical virus load in the lesions was measured with Tzank test and the healing time was recorded on the days 0, 1, 4, 7 and 14.

The mean amount of virus loaded multinucleated cells was 750 before treatment, 465 on the day one, 359 on the day four, 226 on the day seven and 0 on the day 14, indicating a strong topical anti-viral effect. The average topical lesion size which was 1.528 on the day 1, was reduced to 0.683 on the day 4, 0.193 on the day seven and 0 on the day 14, showing complete lesion healing in all the patients within 14 days. No topical reaction or side effects were noted in any of the participants.

For genital herpes study, 60 women with diagnosed recent vaginal herpes were included in the study. The product was applied as a single treatment of 10-ml solution, once a day for 3-consecutive days. The amount of topical virus particles in the vaginal cavity was measured using Tzank test. Lesion size, itching, pain, pH and burning sensation were also recorded over a period of 14 days.

The mean results indicated a very fast reduction in the amount of topical herpes virus which was 645 before treatment; 529 on the day 2; 341 on the day 4; 158 on the day 7 and 0 on the day 14 with 51% reduction in the lesion size on the day 4 and complete healing on the day 14 in all the patients. All other accompanying clinical signs were also reduced. No side effects were noted in any of the participants.

These results prove the topical synergistic anti-viral activity and the absence of toxicity or side-effects of the formulations given in an embodiment of this invention.

The pharmacological, toxicological and clinical results thus indicate that the synergistic compositions of plant extracts rich in tannins can be used as an effective topical antiviral drug without any toxic effect or adverse effect by topical application. The plant extracts rich in tannins obtained from E. purpurea and C. sinensis possess specific anti-protease activity while the plant extracts rich in tannins obtained from M. tenuiflora, A. vulgaris, A. hippocastanum and S. officinalis have the properties to bind with the viral surface glycoproteins. These anti-protease and anti-virus glycoprotein effects are not very strong with the use of individual plant extract as the maximum virus neutralization was less than 40%. However, a 50-50% association of a protease inhibiting plant extract such as E. purpurea and C. sinensis with a virus glycoprotein inhibiting plant extract such as M. tenuiflora, A. vulgaris, A. hippocastanum, A. catechu or S. officinalis showed strong synergistic effect to neutralize almost all the free virus particles present on the surface of the infected cells.

The best synergistic effects were observed with the association of E. purpurea+M. tenuiflora, E. purpurea+A. vulgaris, E. purpurea+C. asiatica and E. purpurea+A. hippocastanum on herpes virus neutralization (above 80%) while E. purpurea+C. sinensis, C. sinensis+A. catechu and C. sinensis+M. tenuiflora were found to neutralize above 80% influenza virus.

These results prove that to stop topical viral growth, it is essential to employ a method so as to inhibit the activities of those proteases which are involved in virus entry into the cells as well as to neutralize the virus glycoproteins so as to simultaneously block the dual system involved in virus host cell interaction.

This is the first time that the specific anti protease activities of E. purpurea and C. sinensis were discovered and the specific virus glycoprotein inhibiting properties of M. tenuiflora, A. vulgaris, C. asiatica, A. hippocastanum and S. officinalis were evaluated. Surprisingly we observed that the inhibition of specific virus proteases and specific virus glycoproteins is essential to neutralize the free virus particles topically to treat topical virus infections. This is the first time that the anti-protease or virus glycoprotein inhibiting properties of plant extracts rich in tannins was discovered. This is also the first time that the synergistic effects of plant extracts rich in tannins on topical virus neutralization is demonstrated.

Further research in our laboratory proved that the plant extracts cited in this disclosure are effective against the entire glycoprotein coat containing virus species.

The compositions and the medicament according to an embodiment of the invention can be applied topically, either as a gel, liquid, spray, ointment, patch, as cotton gauze soaked with the composition according to an embodiment of the invention or as a powder. The composition can be applied as a single or multiple applications per day, preferably 3-4 applications per day for a period of 1 to 10 days depending upon the size of the lesion and the type of viral infection. The plant extracts and subsequent compositions according to an embodiment of the invention can be prepared by mixing different ingredients employing any of the methods or procedures well known in the art.

The plant extracts can be prepared as liquid or dry plant extracts, either as a crude plant extract of the whole plant or of a specific part of the plant, or as a purified extract in the form of a liquid or powder. Extracts can also be enriched in tannins using different methods well known in the art and can also be used as a purified tannin from a plant. Although the experiments were conducted using the most active species of the plant (example Echinacea purpurea), other species of the plant from the same family (family Asteraceae: E. angustifolia, E. pallida) can also be used as the compositions of different species of plants in the same family is very identical.

The plant extracts can also be associated with a carrier system to improve the bioavailability or topical penetration as a powder or liquid. For example, the extract can be mixed with a carrier such as the glycerol, honey, clay, an ointment, water, alcohol, gel or a lotion. They can also be incorporated in a polymer film, in a hydro-gel, in a bandage like cotton bandage or in an antiseptic, anti-inflammatory, antibiotic or wound healing preparation, formulated according to usual methods.

The composition can be formulated as a drug as a medical device or as cosmetics for topical application and preferably as a medical device as the main active ingredients of the preparation act through their mechanical and physical properties without any pharmacological effects on cellular functions.

An embodiment of the invention also relates to a method of treatment of topical viral infection, comprising either the plant extract of E. purpurea or C. sinensis as topical protease inhibitors or M. tenuiflora, A. vulgaris, C. asiatica, A. hippocastanum, A. catechu or S. officinalis, as virus glycoprotein inhibitor alone or in a synergistic association comprising a protease inhibitor plant extract along with one or more virus glycoprotein inhibitor plant extracts, particularly tannin rich plant extracts, for topical application.

For example, to treat influenza virus infection on the throat, an influenza virus helping protease inhibitor plant extract such as E. purpurea can be synergistically associated with an influenza virus glycoprotein inhibitor plant extract such as C. sinensis. To treat herpes virus topical lesion, a herpes virus entry protease inhibitor such as E. purpurea or C. asiatica can be synergistically associated with a herpes virus glycoprotein inhibitor tannin rich plant extract such as A. vulgaris, M. tenuiflora or A. catechu. Although, individual protease inhibiting plant extract or virus glycoprotein inhibiting extract can be used, blocking virus protease on one hand and the virus entry glycoprotein on the other hand is the most logical approach to stop the infection instantly.

The amount of product applied topically can be variable depending upon the size of the lesion or the type of infection between 0.1 to 50 ml per application; for example to treat topical herpes virus lesion, 0.1 ml or a few drops of a liquid solution can be applied topically directly on the lesion. To treat influenza throat virus infection, a liquid product can be spread directly over the throat surface as a spray of 2-6 ml product, 3-4 times a day at the start of treatment for a period of 2-3 days or up to complete recovery. The following examples illustrate embodiments of the invention, but they should not be considered to limit the scope of the invention in any way.

The synergistic effect of the association of at least two plant extracts rich in tannins in preventing and/or curing topical viral infections is apparent from the following examples. The presented examples illustrate embodiments of the invention, but they should not be considered to limit the scope of the invention in any way.

EXAMPLES

Examples of compositions according to embodiments of the invention: In the absence of evidence to the contrary, the quantity of compounds comprised in different compositions is expressed in g/100 g (w/w). Qsp signifies quantity sufficient to produce the amount indicated.

Example 1

Liquid extract of *E. purpurea* (3.0% tannins): 5.4 g
Liquid extract of *C. sinensis* (2.5% tannins): 2.6 g
Water: qsp 100 g

Example 2

Liquid extract of *E. purpurea* (6.8% tannins): 3.5 g
Liquid extract of *C. sinensis* (8.5% tannins): 1.5 g
Glycerol qsp 100 g

Example 3

Synergistic Composition for the Treatment of Throat as a Spray (30-ml Bottle)

Glycerol: 74 g
Honey: 12 g
Dry extract of *E. purpurea*: 0.63 g
Dry extract of *S. officinalis*: 0.15 g
Water qsp 100 g
(Apply as a throat spray at an interval of 30 minutes at the start of treatment 4-5 times and than 3-4 times a day for 3 days).

Example 4

Synergistic Composition the Treatment of Labial Herpes

Honey: 20.0 g
12% tannin rich extract of *A. catechu*: 1.9 g
12% tannin rich extract of *E. purpurea*: 2.6 g
Water: 2.25%
Xanthan gum: 0.1%
Glycerol qsp 100 g
(Apply 3-4 drops on the lesion, 3-4 times a day up to complete healing.

Example 5

Synergistic Composition for the Treatment of Genital Herpes

12% dried plant hydroglycerinated extract of *A. hippocastanum*: 1.2 g
12% dried hydroglycerinated plant extract of *E. purpurea*: 1.8 g
Glycerol as excepient qsp 100 g
(Empty the contents of 1 10-ml tube deep into the vaginal cavity, once a day preferably before night rest, for 3 consecutive days. Repeat the treatment for 3 extra days if required).

Example 6

Synergistic Composition for the Treatment of Throat Infection

Water: 12 g
*C. sinensis*: 1.0 g
*C. asiatica* extract: 6.4 g
Honey qsp 100 g
(Mix 20 ml of the solution in about 80 ml of Luke warm water and gargle 2-3 times a day).

Example 7

Dried whole plant extract of *E. purpura*: 0.74 g
Dried bark extract of *M. tenuiflora*: 0.66 g
Xanthan gum: 0.4 g
Aqua: qsp 100 g.

Example 8

Cosmetic Gel Composition to Treat Open Viral Lesions on the Skin

Honey: 11 g; Glycerin: 6.0 g; Glyceryl polymethacrylate: 2.1 g; Dried extract of *E. purpurea*: 0.52 g, Dried extract of *M. tenuiflora*: 0.33 g, PEG-40: 0.1 g; Xanthan gum: 0.5 g, Paraben as a stabilizer: 0.5 g; Aqua qsp 100 g.
Apply about 0.5 g gel directly on the lesion, 2 times per day for 7-10 consecutive days.

Example 9

Cosmetic Cream Composition for Papilloma Virus Treatment

Water extract of *C. sinensis* containing 8% tannins: 8 g; Water extract of *A. vulgaris* containing 6.5% tannins: 4.2%; Sorbitan sterate: 5.4 g; Squalene: 2.0 g; Octyl octanoate: 2.0 g; Saccharide isomerate: 1.5 g; Caprylic capric triglyceride: 1.5 g; Octyldodecylmyristate: 1.5 g; Dioctylmalate: 1.5 g, Triethanomine: 0.66 g; Sucrose cocoate: 0.6 g; Carbomer 0.55 g; Cetryl alcohol: 0.5 g; Cetyl palmitate: 0.5 g; Glyceryl state: 0.5 g; Phenoxyethanol: 0.36 g; Propylene glycol: 0.20 g; Parabens as stabilizer: 0.02 g; Aqua qsp: 100 g An exemplary embodiment of the present invention provides a synergistic composition capable to simultaneously neutralize both proteases and viral glycoproteins, which are involved in facilitating viral entry or viral attachment to the host cells and in the pathogenicity of glycoprotein enveloped viruses inducing topical infections.

An exemplary embodiment of this invention provides a synergistic composition capable to neutralize both proteases and viral glycoproteins involved in topical infections such as the herpes virus, influenza virus, human papilloma virus, adenovirus, retrovirus and other topical enveloped viruses.

An exemplary embodiment of the present invention provides a synergistic composition capable to neutralize both proteases and viral glycoproteins involved in topical infections such as the cold sores, genital herpes, viral throat infections, eczema herpeticum, human papilloma, exanthems, viral wart lesions and other viral infections where free virus particles are found on the surface of the lesions.

An exemplary embodiment of this invention provides a synergistic composition as a preventive or curative treatment for topical viral infections.

An exemplary embodiment of this invention provides a synergistic composition as a cosmetic or drug or a medical device which is safe, efficient and inexpensive for the treatment of topical viral infections of human and animal bodies.

In at least one embodiment of the present disclosure, the inventor has solved in whole or part of the problems mentioned above.

As previously indicated, hundreds of proteases on infected surface are known but a lot many others remain unknown. It is thus practically impossible to find a specific inhibitor for each protease. Similarly, as there are numerous glycoproteins on the virus coat, it is also extremely difficult to neutralize all the virus glycoproteins at a time.

During his works, the inventor has surprisingly observed that an association of specific tannin rich plant extracts can synergistically neutralizes specific virus glycoproteins and proteases at a time and thus neutralizes topical virus infection at the stage of the initial infection.

The experiments conducted by the inventor clearly show that the topical viral infections cannot be stopped completely if only the viral glycoproteins are neutralized or if only proteases are blocked. This is because there are millions of virus particles on the surface and it is essential to neutralize both these systems at a time to reduce the infection.

Unfortunately, up till now, there is no known drug, or plant extract or tannin having these two basic properties essential to stop topical viral infection. Before this invention, neither it was known that to treat topical viral infection, it is essential to neutralize viral glycoproteins and specific proteases simultaneously, nor that there was any natural or synthetic product directed to block virus glycoproteins and proteases together to treat topical viral infections.

REFERENCES

Cheshenko N et al. Glycoprotein B plays a predominant role in mediating herpes simplex virus type 2 attachments. J Gen Virol. 83, 2247-55, 2002.

Mark G. M. et al. Cellular Proteasome Activity Facilitates Herpes Simplex Virus Entry. Virol. 2008, 82(7): 3381-3390, 2008.

Martínez-Torres F J. Increased presence of matrix metalloproteinases 2 and 9 in short- and long-term experimental herpes simplex virus encephalitis. Neurosci Lett. 368(3): 274-278, 2004.

Kido H. Cellular proteases involved in the pathogenicity of enveloped animal viruses, human immunodeficiency virus, influenza virus A and Sendai virus. Adv Enzyme Regul. 36:325-347, 1996.

Kido H. Proteases essential for human influenza virus entry into cells and their inhibitors as potential therapeutic agents. Curr Pharm Des. 13, 4, 405-414, 2007. HUIE Carmen W. A review of modern sample-preparation techniques for the extraction and analysis of medicinal plants: Modern Sample Preparation Techniques. Analytical and bioanalytical chemistry. 373 (2): 23-30, 2002.

La Frazia S. Antiviral activity of proteasome inhibitors in herpes simplex virus-1 infection: role of nuclear factor-kappaB. Antivir Ther. 11(8):995-1004, 2006.

Liu S et al. Identification of inhibitors of the HIV-1 gp41 six-helix bundle formation from extracts of Chinese medicinal herbs Prunella vulgaris and Rhizoma cibotte. Life Sci.71(15):1779-1791, 2002.

Patick et al. protease inhibitors as antiviral agents. Clin Microbiol Review, Vol. 11, No 4, 614-627, 1998.

Reed and Muench. A simple method for estimating fifty percent end points. Am J Hyg. 27:493-497, 1938.

Sailer R. et al. Combined herbal preparation for topical treatment of Herpes labialis. Forsch Komplementarmed Klass Naturheilkd. 8(6):373-82, 2001.

Urban M. Viral infection: Merck Manual Home edition in www.nlm.nih.gov/medineplus/viral infections.html. pp 1-5, 2009.

Witvrouw M. Sulfated polysaccharides extracted from sea algae as potential antiviral drugs. Gen Pharmacol. 29(4): 497-511, 1997.

What is claimed is:

1. A method of treating herpes or influenza in a human in need thereof consisting essentially of administering to said human therapeutically effective amounts of *Echinacea Pupurea* extract and *Mimosa Tenuiflora* extract to treat said herpes or influenza in said human.

2. A method of treating herpes or influenza in a human in need thereof consisting essentially of administering to said human therapeutically effective amounts of *Echinacea Pupurea* extract and *Camellia sinensis* extract to treat said herpes or influenza in said human.

3. A method of treating herpes or influenza in a human in need thereof consisting essentially of administering to said human therapeutically effective amounts of *Acacia catechu* extract and *Camellia sinensis* extract to treat said herpes or influenza in said human.

4. A method of treating herpes or influenza in a human in need thereof consisting essentially of administering to said human therapeutically effective amounts of *Mimosa Tenuiflora* extract and *Camellia sinensis* extract to treat said herpes or influenza in said human.

5. A method of treating herpes or influenza in a human in need thereof consisting essentially of administering to said human therapeutically effective amounts of *Echinacea Pupurea* extract and *Acacia catechu* extract to treat said herpes or influenza in said human.

* * * * *